United States Patent [19]
Levy et al.

[11] Patent Number: 6,136,602
[45] Date of Patent: Oct. 24, 2000

[54] OLIGONUCLEOTIDES SPECIFIC FOR THE MARORAB OPERON

[75] Inventors: Stuart B. Levy, Boston; Eric Von Hofe, Wellesley, both of Mass.

[73] Assignees: Hybridon, Inc.; Trustees of Tufts College

[21] Appl. No.: 09/027,130

[22] Filed: Feb. 20, 1998

Related U.S. Application Data

[60] Provisional application No. 60/038,663, Feb. 21, 1997.

[51] Int. Cl.$^7$ .............................. C07H 21/04; C12Q 1/68
[52] U.S. Cl. ............................. 435/375; 435/6; 435/455; 435/320.1; 435/325; 435/252.1; 435/252.33; 536/23.1; 536/24.1; 536/24.3; 536/24.5
[58] Field of Search ................................ 435/6, 455, 375, 435/320.1, 325, 252.1, 252.33; 536/23.1, 24.1, 24.3, 24.5; 514/44

[56] References Cited

U.S. PATENT DOCUMENTS 5,817,793  10/1998  Levy ...................................... 536/24.1

FOREIGN PATENT DOCUMENTS

| 0 472 434 A2 | 2/1992 | European Pat. Off. . |
| WO 93/13740 | 7/1993 | WIPO . |
| WO 94/02498 | 2/1994 | WIPO . |
| WO 94/05810 | 3/1994 | WIPO . |

OTHER PUBLICATIONS

Uhlmann et al. "Antisense Oligonucleotides: A New Therapeutic Principle" Chemical Reviews vol. 90(4): 543–584, Jun. 1990.
Agrawal. "Antisense Oligonucleotides: Towards Clinical Trials" TIBTECH vol. 14:376–387, Oct. 1996.
Branch. "A Good Antisense is Hard to Find" TIBS vol. 23: 45–50, Feb. 1998.
Blattner F.R., et al. EMBL Nucleotide Sequence Database Jan. 29, 1997. Accession No. AE000250. *E. coli* Mar R, Mar A, and Mar B genes.
Agrawal, Sudhir "Antisense Oligonucleotides as Antiviral Agents", TIBTECH, (1992) vol. 10 pp. 152–158.
Blattner, Frederick R. et al. (1997) "The Complete Genome Sequence of *Escherichia Coli* K–12", Science vol. 277 pp. 1453–1462.
Cohen, Seth P. et al. (1993) "A Multidrug Resistance Regulatory Chromosomal Locus Is Widespread amoung Enteric Bacteria", The Journal of Infectious Diseases vol. 168 pp. 484–488.
Cohen, Seth P. et al. (1993) "Genetic and Functional Analysis of the Multiple Antibiotic Resistance (mar) Locus in *Escherichia Coli*" Journal of Bacteriology vol. 175, No. 5 pp. 1484–1492.
Gambino, Laura et al. (1993) "Overexpression of the MarA Positive Regulator Is Sufficient To Confer Multiple Antibiotic Resistance in *Escherichia Coli*" Journal of Bacteriology vol. 175 pp. 2888–2894.
Goldman, John D. et al. (1996) "Multiple Antiobiotic Resistance (mar) Locus Protects *Escherichia Coli* from Rapid Cell Killing by Fluoroquinolones" Antimicrobial Agents and Chemotherapy vol. 40, No. 5 pp. 1266–1269.
Hoke, Glenn D. et al. (1991) "Effects of Phosphorothioate Capping on Antisense Oligonucleotide Stability, Hybridization and Antiviral Efficacy Versus Herpes Simplex Virus Infection", Nucleic Acids Research vol. 19, No. 20 pp. 5743–5748.
Metalev, Valeri et al. (1994) "Study of Antisense Oligonucleotide Phosphorothioates Containing Segments of Oligodeoxynucleotides and 2 O Methyloligoribonucleotides" Bioorganic & Medicinal Chemistry Letters vol. 4 No. 14 pp., 2929–2934.
White, D.G., et al. (1997) "Inhibition of the Multiple Antibiotic Resistance (mar) Operon in *Escherichia Coli* by Antisense DNA Analogs" Antimicrobial Agents and Chemotherapy vol. 41 pp. 2699–2704.
White, D.G., et al. (1997) "Inhibition of the Multiple Antibiotic Resistance (mar) Operon in *Escherichia Coli* by Antisense DNA Analogs" Abstracts of the General Meeting of the American Society for Microbiology Vo. 0 No. A–69 May 1997, Washington, D.C.

*Primary Examiner*—Robert A. Schwartzman
*Assistant Examiner*—Sean McGarry
*Attorney, Agent, or Firm*—Lahive & Cockfield

[57] ABSTRACT

Disclosed are synthetic oligonucleotides complementary to a transcript of the marORAB operon which inhibit expression of a gene in the operon. Also disclosed are methods of reducing bacterial resistance to antibiotics, and pharmaceutical formulations containing marORAB-specific oligonucleotides of the invention.

21 Claims, 2 Drawing Sheets

OLIGONUCLEOTIDES SPECIFIC FOR THE MARORAB OPERON

RELATED APPLICATION

This application claims priority to the U.S. Provisional application Ser. No. 60/038,663, entitled "OLIGONUCLEOTIDES SPECIFIC FOR THE marORAB OPERON AND METHODS OF THEIR USE", filed Feb. 21, 1997, the contents of which are expressly incorporated by reference.

BACKGROUND OF THE INVENTION

This invention relates to the control of prokaryotic multidrug susceptibility. More specifically, this invention relates to the use of oligonucleotides for the treatment of diseases, disorders, and conditions associated with drug resistance in bacteria.

Bacterial antibiotic and antimicrobial resistance has been recognized since the advent of antimicrobial agents. In the past, the appearance of resistant microorganisms has been addressed by the continued availability of effective alternative drugs. As reported by Neu (*Science* (1992) 257:1064–1073), the situation has recently changed dramatically, leading to increasing morbidity and mortality. The growing number of pathogens resistant to multiple, structurally unrelated drugs, and the fact that no new class of antimicrobials is likely to be introduced before the end of the decade, have been blamed for the present crisis of clinical and epidemiologic significance (see, e.g. Neu, supra). Thus, as discussed extensively in the medical and scientific literature, there is a growing need to formulate effective therapeutic approaches to counter the emergence of novel bacterial strains resistant to antibiotics.

Resistance to an antimicrobial agent may be an inherent property of the infecting organism, or may result from mutation or from transfer of an extrachromosomal genetic determinant, such as plasmids and transposons, followed by selection of resistant organisms. In recent years there has been increased interest in the role of chromosomal sequences involved in conferring antibiotic resistance. A novel chromosomal stress response locus, the multiple antibiotic resistance (mar) locus has been shown to control the expression of chromosomal genes involved in intrinsic multidrug susceptibility/resistance to multiple, structurally different antibiotics and other noxious agents in Escherichia coli and in other members of the Enterobacteriaceae family (Cohen et al. (1988) *J. Bacteriol.* 170:5416–5422; Cohen et al. (1993) *J. Infec. Dis.* 168:484–488).

The mar locus has been reported to include two transcriptional units, marC and marRAB. Each unit is divergently transcribed from a central regulatory region, marO (Cohen et al. (1993) *J. Bacteriol.* 175:1484–1492; and Goldman, J. et al. (1996) *Antimicrobiol. Agents Chemo.* 40:1266–1269). Both operons, marORAB and marC are necessary for the full expression of the Mar phenotype. Transcription of the marORAB operon is inducible two to three fold by tetracycline, chloramphenicol, salicylate, and other structurally unrelated compounds (Cohen et al., supra). Activated cells become resistant not only to multiple unrelated antibiotics but also to oxidative stress agents and organic solvents (Cohen et al., supra; George, et al. (1983) *J. Bacteriol.* 155:531–540; George et al. (1996) *FEMS Micro. Let.* 139:1–10).

In the presence of selective agents (e.g., tetracycline, chloramphenicol, nalidixic acid, rifampin, penicillin, and cephalosporin) Mar mutants arise spontaneously at a frequency of $10^{-7}$ (George, et al., *J. Bacteriol.* supra). Such mutants have been reported to favor the accumulation of secondary mutations leading to the expression of higher levels of resistance to novel or improved antimicrobial agents. For example, Mar mutants have recently been found among fluoroquinolone-resistant clinical isolates of *E. coli* (Maneewannakul et al.(1996) *Antimicrob. Agents Chemo.* 38:542–546).

Characterization of several Mar mutant resistant strains has revealed constitutive transcription of mRNA from the marORAB operon as a result of various mutations within that operon (Cohen et al., supra). Consistent with these findings, the disruption of the mar locus has correlated with the complete loss of resistance. The resistance phenotype has been completely reversed to susceptibility by insertion of Tn5, a transposon element, into the marA gene of the *E. coli* chromosome. (George et al. (1983) *J. Bacteriol.* 155:541–548).

A promising new approach to antimicrobial therapy lies in the use of short synthetic strands of nucleic acids, called antisense oligonucleotides, to control gene expression. Inhibition of gene expression by antisense oligonucleotides relies at least in part, on the ability of the oligonucleotide to bind a complementary messenger RNA sequence, thereby preventing its translation (see generally, Agarwal (1992) *Trends in Biotech.* 10:152; Wagner et al.(1 994) *Nature* 372:333–335; and Stein et al. (1993) *Science* 261:1004–1012). Synthetic oligonucleotides administered exogenously compose an alternate class of therapeutic agents and have been used successfully in both prokaryotic and eucaryotic systems.

Antisense oligonucleotides have been developed as antiparasitic agents, although none have been demonstrated to reverse the drug resistant phenotype of a drug resistant parasite strain. PCT publication No. WO 93/13740 discloses the use of antisense oligonucleotides directed to nucleic acids encoding the dihydrofolate reductase-thymidilate synthase gene of P. falciparum to inhibit propagation of drug-resistant malarial parasites. Rapaport et al. (*Proc. Natl. Acad. Sci.* (*USA*) (1992) 89:8577–8580) teaches inhibition of the growth of chloroquine-resistant and chloroquine-sensitive P. falciparum in vitro using oligonucleotides directed to the dihydrofolate reductase-thymidylate synthase gene. PCT publication No. WO 94/12643 discloses antisense oligonucleotides directed to nucleic acids encoding a carbamoyl phosphate synthetase of P. falciparum. Tao et al. (*Antisense Res. Dev.* (1995) 5:123–129) teaches inhibition of propagation of a schistosome parasite by antisense oligonucleotides. Early experiments by Jayaraman showed that an antisense oligonucleotide complementary to the Shine-Delagamo ribosomal docking sequence of *E. coli* 16S rRNA, inhibited translation of bacterial mRNA in cell-free extracts derived from *E. coli* (Jayaraman (1996) *Proc. Natl. Acad. Sci* (*USA*) 93:709–713). Furthermore, experiments were conducted by Gasparro et al. using a photoactivatable antisense DNA construct to suppress ampicillin resistance in *E. coli* (Gasparro et al. *Antisense Res. Dev.* (1991) 1:117–140)). More recently, experiments utilizing antisense oligodeoxyribonucleotide phosphorothioates have shown the successful inhibition of the growth of a wild-type and drag resistant strain of Mycobacterium smegmatis (Rapaport et al. (1996) *Proc. Natl. Acad. Sci.* (*USA*) 93:709–713).

Bacteria have been known to mutate extensively, resulting in a large number of strains which have become resistant to most drugs presently available. In addition, new resistant bacterial strains are likely to develop as the time progresses. Thus, there is a continued need for development of additional therapeutic agents and effective methods to treat these bacterial infections. Inactivation or suppression of the multiple antibiotic resistance operon would ideally make some prokaryotes more susceptible to a larger number of antimicrobial agents and environmental stresses, thus providing novel means to counter increased bacterial resistance.

SUMMARY OF THE INVENTION

The invention disclosed herein satisfies this need. The present inventors have discovered that antisense oligonucleotides that are complementary to sequences found in the marORAB operon can inhibit or suppress the expression of one or more genes within that operon, thereby making bacteria more susceptible to a larger number of antimicrobial agents and environmental stresses.

This discovery has been exploited to develop the present invention which includes antisense oligonucleotides directed to mRNA derived from the marORAB operon sequences which specifically inhibit or suppress the expression of one or more genes within that operon, and which are therefore useful both as therapeutic agents and as tools to elucidate the role and biological significance of the marORAB operon sequences.

In one aspect, the invention provides a synthetic oligonucleotide complementary to a transcript of the marORAB operon which inhibits the expression of a gene in the operon.

As used herein, the term "operon" is a unit of bacterial gene expression and regulation. Typically an operon includes nucleic acid and control elements in the nucleic acid which may be recognized by regulators of gene products. In the case of marORAB operon, the nucleic acid includes a regulatory region, designated marO, containing a promoter and an AUG start codon for rightward transcription of the loci designated marR, marA and marB.

For purposes of the invention, the term "transcript" is used to refer to ribonucleic acid transcribed from DNA, some of which is capable of serving as a substrate for the translation of one or more peptide products.

As used herein, the term "locus" refers to a position on a chromosome at which nucleic acid encoding a particular gene or genes reside. The nucleic acid comprises a start codon and at least one codon encoding an amino acid residue. Typically, a locus is transcribed to produce at least one mRNA transcript which in turn may be translated into a peptide.

As used herein, the term "synthetic oligonucleotide" refers to chemically synthesized polymers of nucleotides covalently attached by internucleotide linkages. The term "internucleotide linkage" is used to refer to the covalent bonding between nucleotides which are thus attached via at least one 5' to 3' internucleotide linkage.

In some embodiments of the invention the oligonucleotide contains at least one internucleotide linkage selected from the group consisting of alkylphosphonates, phosphorothioates, phosphorodithioates, alkylphosphonothicates, phosphoramidates, phosphate esters, carbamates, acetamidate, carboxymethyl esters, carbonates, and phosphate triesters. In some other embodiments, the oligonucleotide contains, in addition to an internucleotide linkage selected from the linkages recited, at least one phosphothioate internucleotide linkage.

In some embodiments, the oligonucleotides contain at least one deoxyribonucleotide, at least a ribonucleotide, or both deoxyribonucleotide(s) and ribonucleotide(s).

In some embodiments, the synthetic oligonucleotide is from about 15 to about 50 nucleotides in length. In preferred embodiments, these oligonucleotides contain from about 15 to about 21 nucleotides.

In some particular embodiments of the invention, marORAB oligonucleotides have a nucleotide sequence selected from the group consisting of SEQ ID NO:1, NO:2, NO:3, NO:4, NO:5, and NO:6.

Another aspect of the invention provides a method of inhibiting the expression of the marORAB operon comprising the step of contacting a transcript of marORAB operon with a synthetic oligonucleotide complementary to the transcript. In some embodiments of the invention, the oligonucleotide is complementary to a locus selected from the group consisting of marO, marO/R, marR, marR/A, and marA. In yet other embodiments of the invention, the oligonucleotide comprises a nucleotide sequence selected from the group consisting of SEQ ID NO:1, NO:2, NO:3, NO:4, NO:5, and NO:6.

An additional aspect of the invention provides a method of reducing bacterial resistance to an antibiotic by exposing a resistant bacterium to synthetic oligonucleotide complementary to a transcript of the marORAB operon. The bacterium further may be treated with an antibiotic.

The term "antibiotic" is art recognized and includes a composition which decreases the viability or which inhibits the growth or reproduction of microorganisms. As used in this disclosure, an antibiotic is further intended to include an antimicrobial or bactericidal agent.

In an additional embodiment of the invention the oligonucleotide is complementary to a transcript of a locus selected from the group consisting of marO, marO/R, marR, marR/A, and marA. In yet another embodiment of the invention, the oligonucleotide comprises a nucleotide sequence selected from the group consisting of SEQ ID NO:1, NO:2, NO:3, NO:4, NO:5, and NO:6.

In an additional embodiment, bacteria are contacted with at least two synthetic oligonucleotides selected from the group consisting of SEQ ID NO:1, NO:2, NO:3, NO:4, NO:5, and NO:6.

Another aspect of the invention pertains to a method of treating a bacterial infection in a subject by administering to the subject a therapeutic amount of a synthetic oligonucleotide complementary to a transcript of the marORAB operon which is effective in reducing bacterial resistance to antibacterial agent.

In one embodiment of the invention, the oligonucleotide is complementary to a transcript of a gene or locus selected from the group consisting of marO, marO/R, marR, marR/A, and marA. In an additional embodiment of the invention the oligonucleotide includes a nucleotide sequence selected from the group consisting of SEQ ID NO:1, NO:2, NO:3, NO:4, NO:5, and NO:6.

An additional aspect of the invention is a pharmaceutically acceptable composition comprising a synthetic oligonucleotide complementary to a transcript of marORAB operon nucleic acid which inhibits the expression of one or more genes in the operon, and a physiologically acceptable carrier.

As used herein, the term "pharmaceutically acceptable" means a non-toxic material that does not interfere with the effectiveness of the biological activity of the active ingredient(s). The term "physiologically acceptable" refers to a non-toxic material that is compatible with a biological system such as a cell, cell culture, tissue, or organism.

In one embodiment of the invention, the oligonuclectide is complementary to a locus selected from the group consisting of marO, marO/R, marR, marR/A, and marA.

In yet another embodiment, the oligonucleotide consists essentially of SEQ ID NO:1, NO:2, NO:3, NO:4, NO:5, and NO:6.

BRIEF DESCRIPTION OF THE DRAWINGS

The foregoing and other objects of the present invention, the various features thereof, as well as the invention itself may be more fully understood from the following description, when read together with the accompanying drawings in which.

DETAILED DESCRIPTION OF THE PREFERRED EMBODIMENTS

The present invention provides antisense oligonucleotides specific for marORAB operon nucleic acid which are useful in treating diseases and disorders associated with drug resistance in prokaryotes. Antisense oligonucleotides of the invention are also useful for determining the role of marORAB sequences in pathogenicity, and more specifically, in processes where drug resistance is involved.

MarORAB sequences have been reported in *E. coli* (George et al.(1983) *J. Bacieriol.* supra) in Salmonella, Shigella, Klebsiella, Citrobacter, Hafnia, and Enterobacter bacterial species (Cohen et al. (1993) *J. Infect. Dis.* 168:484–488). In addition, DNA-relatedness studies suggest that enteric bacteria in which the marORAB regulatory operon was found to be conserved may be only a fraction of those in which marORAB-like sequences may be present. (Cohen et al. ibid.).

Figure 1:
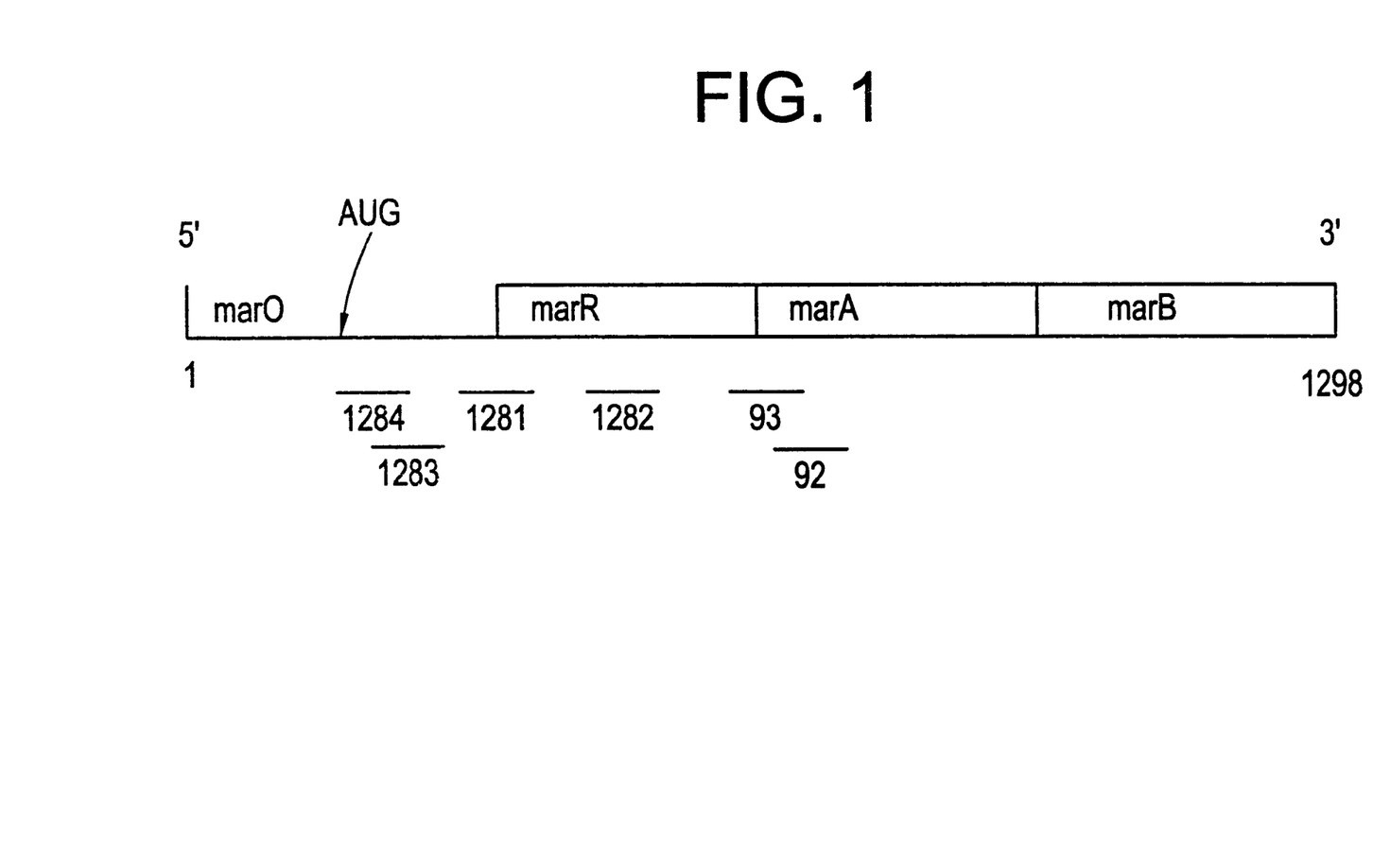
FIG. 1 is a schematic representation of the marORAB operon, including the approximate location of sequences targeted by representative oligonucleotides of the invention.

The marORAB locus at 34 min (1,636 kbp) on the *E. coli* chromosome map has been cloned and sequenced, and its regulation has been studied. (Cohen et al. ibid; and Hachler et al. (1991) *J. Bacteriol.* 173:5532–5538). As shown in FIG. 1, the operon includes a regulatory region, designated marO, containing a promoter-operator region for the rightward transcription of the marR, marA and the marB genes as well as the AUG start codon. The proteins encoded by these genes are MarR, a repressor protein (Cohen et al. ibid.), MarA, a positive regulator protein whose overexpression leads to multidrug resistance, and MarB, a small protein which is required for the full resistance phenotype but whose function is yet unknown (George *J. Bacteriol.* supra; Yan et al. *Abstr.* 1992 *Gen. Meet. Am. Soc. Microbiol.* A-26, p.5).

The oligonucleotides of the invention are directed to any portion of the marORAB operon nucleic acid sequence that effectively acts as a target for inhibiting the expression of the genes within the marORAB operon.

FIG. 1 shows some non-limiting regions of the operon to which oligonucleotide of the invention may be directed. The nucleotide sequences of some representative, non-limiting oligonucleotides specific for the marORAB operon are listed below in TABLE 1.

One of skill in the art, knowing the nucleotide sequence of the marORAB operon (Cohen et al. (1993) *J. Bacteriol.* supra) could prepare other oligonucleotides directed to these regions that inhibit the expression of one or more genes in the operon. For example, other sequences targeted specifically to marORAB nucleic acid can be selected based on their ability to be cleaved by RNase H.

Preferred antisense oligonucleotides useful in the practice of the invention and suitable for use in therapeutic compositions of the invention are particularly active in inhibiting the expression of one or more genes in the marORAB operon. As used herein, the term oligonucleotide includes polymers of two or more ribonucleotides, deoxyribonucleotides, 2' substituted ribonucleotides or deoxyribonucleotides or any combinations of monomers thereof, such monomers being (connected together via 5' to 3' linkages which may include any of the linkages that are known in the antisense oligonucleotide art.

The term oligonucleotide also encompasses such polymers having chemically modified bases or sugars and/or having additional substituents including without limitation, lipophilic groups, intercalating agents, diamines adamantane and others. For example, oligonucleotides used in accordance with the invention may comprise other than phosphodiester internucleotide linkages between the 5' end of one nucleotide and the 3' end of another nucleotide in which the 5' nucleotide phosphate has been replaced with any number of chemical groups, such as a phosphorothioate. The phosphorothioate linkages may be mixed Rp and Sp enantiomers, or they may be stereoregular or substantially stereoregular in either Rp or Sp form (see Iyer et al. (1995) *Tetrahedron Asymmetry* 6:1051–1054).

TABLE 1

| OLIGO | TARGETED SITE | SEQUENCE (5' to 3') | SEQ ID NO: |
|---|---|---|---|
| 92 | marA | GCGTCTGGACATCGTCAT | 1 |
| 93 | marA | ATCGTCATAGCTCTT | 2 |
| 1281 | marOR | CTTTTCACATTAGTTGCCC | 3 |
| 1282 | marR | GCGCTTGTCATTCGGGTTC | 4 |
| 1283 | marO | GTAATTAGTTGCAGAGGATA | 5 |
| 1284 | marO | TAGTTGCAGGAGATAATATTG | 6 |

Oligonucleotides with phosphorothioate linkages can be prepared using methods well known in the field such as phosphoramidite (see, e.g., Agrawal et al. (1988) *Proc. Natl. Acad. Sci.* (*USA*) 85:7079–7083) or by H-phosphonate (see, e.g., Froehler (1986) *Tetrahedron Lett.* 27:5575–5578) chemistry. The synthetic methods described in Bergot et al. (*J. Chromatog.* (1992) 559:35–42) can also be used. Examples of other chemical groups include alkylphosphonates, phosphorodithioates, alkyl phosphonothioates, phosphoramidates, carbamates, acetamidate, carboxymethyl esters, carbonates, and phosphate triesters or any combinations thereof. For example, U.S. Pat. No. 5,149,797 describes traditional chimeric oligonucleotides having a phosphorothioate core region interposed between methylphosphonate or phosphoramidate flanking regions. PCT Application No. PCT US96/13371, filed on Aug. 31, 1996, discloses "inverted" chimeric oligonucleotides comprising one or more nonionic oligonucleotide region (e.g. alkylphosphonate and/or phosphoramidate and/or phosphotriester internucleoside linkage) flanked by one or more region of oligonucleotide phosphorothioate. Various oligonucleotides with modified internucleotide linkages can be prepared according to known methods (see, e.g., Goodchild (1990) *Bioconjugate Chem.* 2:165–187; Agrawal et al., (1988) *Proc. Natl. Acad. Sci.* (*USA*) 85:7079–7083;

Uhlmann et al. (1990) *Chem. Rev.* 90:534–583; and Agrawal et al. (1992) *Trends Biotechnol.* 10:152–158.

Examples of modifications to sugars include modifications to the 2' position of the ribose moiety which include but are not limited to 2'-O-substituted with an -O-lower alkyl group containing 1–6 saturated or unsaturated carbon atoms, or with an -O-aryl, or allyl group having 2–6 carbon atoms wherein such -O-alkyl, aryl or allyl group may be unsubstituted or may be substituted, (e.g., with halo, hydroxy, trifluoromethyl cyano, nitro acyl acyloxy, alkoxy, carboxy, carbalkoxyl, or amino groups), or with an amino, or halo group. None of these substitutions are intended to exclude the native 2'-hydroxyl group in the case of ribose or 2'-H- in the case of deoxyribose. PCT Publication No. WO 94/02498 discloses traditional hybrid oligonucleotides having regions of 2'-O-substituted ribonucleotides flanking a DNA core region. P(CT Application No. PCT US96/13371, filed on Aug. 31, 1996, discloses an "inverted" hybrid oligonucleotide which includes an oligonucleotide comprising a 2'-O-substituted (or 2' OH, unsubstituted) RNA region which is in between two oligodeoxyribonucleotide regions, a structure that "inverted relative to the "traditional" hybrid oligonucleotides.

Other modifications include those which are internal or are at the end(s) of the oligonucleotide molecule and include additions to the molecule at the internucleoside phosphate linkages, such as cholesteryl or diamine compounds with varying numbers of carbon residues between the two amino groups, and terminal ribose, deoxyribose and phosphate modifications which cleave, or crosslink to the opposite chains or to associated enzymes or other proteins which bind to the bacterial genome. Examples of such modified oligonucleotides include oligonucleotides with a modified base and/or sugar such as arabinose instead of ribose, or a 3', 5'-substituted oligonucleotide having a sugar which, at one or both its 3' and 5' positions is attached to a chemical group other than a hydroxyl or phosphate group (at its 3' or 5' position). Other modified oligonucleotides are capped with a nuclease resistance-conferring bulky substituent at their 3' and/or 5' end(s), or have a substitution in one or both nonbridging oxygens per nucleotide. Such modifications can be at some or all of the internucleoside linkages, as well as at either or both ends of the oligonucleotide and/or in the interior of the molecule (reviewed in Agrawal et al. (1992) *Trends Biotechnol.* 10:152–158).

Preferably, oligonucleotides used in accordance with the invention will have from about 7 to about 50 nucleotides, more preferably from about 12 to 35 nucleotides, e.g. 12 to about 30, and most preferably from about 15 to about 21 nucleotides. Such oligonucleotides are preferably complementary to at least a portion of the targeted mRNA transcript of the marORAB operon such that the oligonucleotide is capable of hybridizing or otherwise associating with at least a portion of such mRNA transcript under physiological conditions. Hybridization is ordinarily the result of base-specific hydrogen bonding between complementary strands of mRNA transcript preferably to form Watson-Crick or Hoogsteen base pairs, although other modes of hydrogen bonding, as well as base stacking can also lead to hybridization.

Without being limited to any theory or mechanism, it is generally believed that the activity of oligonucleotides used in accordance with this invention depends on the binding of the oligonucleotide to the target nucleic acid (e.g. to at least a portion of an mRNA transcript thereof), thus disrupting the function of the target, either by hybridization arrest or by destruction of target RNA by RNase H (the ability to activate RNase H when hybridized to RNA). Such hybridization under physiological conditions is measured as a practical matter by observing interference with the function of the nucleic acid sequence.

Thus, a preferred oligonucleotide used in accordance with the invention is capable of forming a stable duplex (or triplex in the Hoogsteen pairing mechanism) with the target nucleic acid, activate RNase H thereby causing effective destruction of the target RNA molecule transcript, and in addition is capable of resisting nucleolytic degradation (e.g. endonuclease and exonuclease activity) in vivo. A number of the modifications to oligonucleotides described above and others which are known in the art specifically and successfully address each of these preferred characteristics.

The synthetic antisense oligonucleotides of the invention in the form of a therapeutic formulation are useful in treating diseases, and disorders, and conditions associated with drug resistance in prokaryotes. Such formulations include a physiologically and/or pharmaceutically acceptable carrier. The characteristics of the carrier will depend on the route of administration. Such a composition may contain, in addition to the synthetic oligonucleotide and carrier, diluents, fillers, salts, buffers, stabilizers, solubilizers, and other materials well known in the art. The pharmaceutical composition of the invention may also contain other active factors and/or agents which enhance inhibition of the expression of marORAB operon sequences or which will reduce drug resistance in prokaryotes. For example, combinations of synthetic oligonucleotides, each of which is directed to transcripts from different regions of the marORAB operon, may be used in the pharmaceutical compositions of the invention. The pharmaceutical composition of the invention may further contain penicillins, cephalosporins, aminoglycosides, sulfonamides, macrolides, tetracyclines, lincosides, quinolones, chloramphenicol, vencomycin, metronidazole, rifampin, isoniazid, fm-butylethambutol, spectinomycin, trimethoprim, sulfamethoxazole, and others.

Such additional factors and/or agents may be included in the pharmaceutical composition to produce a synergistic effect with the synthetic oligonucleotide of the invention, or to minimize side-effects caused by the synthetic oligonucleotide of the invention.

The pharmaceutical composition of the invention may be in the form of a liposome in which the synthetic oligonucleotides of the invention are combined, in addition to other pharmaceutically acceptable carriers, with amphipathic agents such as lipids which exist in aggregated form as micelles, insoluble monolayers, liquid crystals, or lamellar layers which are in aqueous solution. Suitable lipids for liposomal formulation include, without limitation, monoglycerides, diglycerides, sulfatides, lysolecithin, phospholipids, saponin, bile acids, and the like. One particularly useful lipid carrier is lipofectin. Preparation of such liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323. The pharmaceutical composition of the invention may further include compounds such as cyclodextrins and the like which enhance delivery of oligonucleotides into cells, as described by Habus et al. (*Bioconjug. Chem.* (1995) 6:327–3331), or slow release polymers.

As used herein, the term "therapeutically effective amount" means the total amount of each active component of the pharmaceutical composition or method that is sufficient to show a meaningful patient benefit, i.e., healing of conditions associated with bacterial drug resistance. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of one or more of the synthetic oligonucleotides of the invention is administered to a subject afflicted with a disease, disorder or condition associated with bacterial drug resistance. The synthetic oligonucleotide of the invention may be administered in accordance with the method of the invention either alone of in combination with other known therapies. When co-administered with one or more other therapies, the synthetic oligonucleotide of the invention may be administered either simultaneously with the other treatment(s), or sequentially. If administered sequentially, the attending physician will decide on the appropriate sequence of administering the synthetic oligonucleotide of the invention in combination with the other therapy.

Administration of the synthetic oligonucleotide of the invention used in the pharmaceutical composition or to practice the method of the present invention can be carried out in a variety of conventional ways, such as, for example, oral ingestion, inhalation, or cutaneous, subcutaneous, intramuscular, or intravenous injection.

When a therapeutically effective amount of synthetic oligonucleotide of the invention is administered orally, the synthetic oligonucleotide will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% synthetic oligonucleotide and preferably from about 25 to 90% synthetic oligonucleotide. When administered in liquid form, a liquid carrier such as water, petroleum, oils of animal or plant origin such as peanut oil, mineral oil, soybean oil, sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of the synthetic oligonucleotide and preferably from about 1 to 50% synthetic oligonucleotide.

When a therapeutically effective amount of synthetic oligonucleotide of the invention is administered by intravenous, subcutaneous, intramuscular, intraocular, or intraperitoneal injection, the synthetic oligonucleotide will be in the form of a pyrogen-free, parenterally acceptable aqueous solution. The preparation of such parenterally acceptable solutions, having due regard to pH, isotonicity, stability, and the like, is within the skill in the art. A preferred pharmaceutical composition for intravenous, subcutaneous, intramuscular, intraperitoneal, or intraocular injection should contain, in addition to the synthetic oligonucleotide, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

The amount of synthetic oligonucleotide in the pharmaceutical composition of the present invention will depend upon the nature and severity of the condition being treated, and on the nature of prior treatments which the patent has undergone. Ultimately, the attending physician will decide the amount of synthetic oligonucleotide with which to treat each individual patient. Initially, the attending physician will administer low doses of the synthetic oligonucleotide and observe the patient's response. Larger doses of synthetic oligonucleotide may be administered until the optimal therapeutic effect is obtained for the patient, and at that point the dosage is not increased further. It is contemplated that the dosages of the pharmaceutical compositions administered in the method of the present invention should contain about 0.1 to 5.0 mg/kg body weight per day, and preferably 0.1 to 2.0 mg/kg, body weight per day. When administered systemically, the therapeutic composition is preferably administered at a sufficient dosage to attain a blood level of oligonucleotide from about 0.01 $\mu$M to about 10 $\mu$M.

The duration of intravenous therapy using the pharmaceutical composition of the present invention will vary, depending on the severity of the disease being treated and the condition and potential idiosyncratic response of each individual patient. Ultimately the attending physician will decide on the appropriate duration of intravenous therapy using the pharmaceutical composition of the present invention. Some diseases lend themselves to acute treatment while others require longer term therapy.

Antisense oligonucleotides of the invention specific for the marORAB operon sequences are useful in determining the role of these sequences in pathogenicity, and more specifically in processes in which drug resistance is involved. For example, the efficacy of antisense technology in inhibiting bacterial drug resistance was measured in comparison to that of the wild type repressor marR. To measure the inhibitory effect of wild type MarR, DNA vectors containing marR sequences were introduced and expressed in two different fusion cell lines containing lac Z sequences under the control of the marORAB operon. The cell lines used are wild type AG 100 (George et al. (1983), supra) and the Mar mutant AG 102. Wild type repressor MarR reduced lacZ expression from the 2 different fusions by 9–47 fold depending on the bacterial strain assayed.

Subsequently, to test the feasibility of using antisense technology to inhibit the expression of sequences under the control of the marORAB operon, a DNA vector containing both the marR and the marA genes cloned in the antisense direction (pKMN23), was tested for its ability to inhibit the production of β-galactosidase activity from marA-lacZ translational fusions. More specifically, pKMN23 was tested in KMN14 (marO*RA-lacZ) and in KMN18 (marORA-lacZ) cells. Both KMN14 and KMN18 are translational fusion cell lines containing marA sequences in the same translational fusion as LacZ. KMN14 is a mutant containing, a mar-R2 mutation in the marR region. The results are shown in TABLE 2.

TABLE 2

| STRAIN | GENE TRANSIENTLY EXPRESSED | β-GAL ACTIVITY | FOLD REDUCTION |
|---|---|---|---|
| KMN14 (marO*RA-lacZ) | | 5130 | — |
| | marR | 550 | 9.3 |
| | mutant marR | 4278 | 1.2 |
| | anti-marA | 950 | 5.4 |

TABLE 2-continued

| STRAIN | GENE TRANSIENTLY EXPRESSED | β-GAL ACTIVITY | FOLD REDUCTION |
|---|---|---|---|
| KMN18 (marORA-lacZ) | — | 2741 | — |
| | marR | 59 | 46.5 |
| | mutant marR | 1659 | 1.7 |
| | anti-marA | 56 | 48.9 |

As shown above, plasmids containing antisense marA sequences effectively reduced LacZ expression from the fusions by 5–49 fold, thus achieving an inhibitory effect comparable to that observed when adding wild type repressor MarR.

To establish further the inhibitory efficacy of antisense marA sequences, KMN23 (the same DNA vector described above, containing both the marR and the marA genes cloned in the antisense direction) was also expressed in the presence of various antibiotics (tetracycline (Tet), chloramphenicol (Cml), ampicillin (Amp) and rifampicin (Rif). The effect of KMN23 was assessed by measuring cell growth inhibition by the gradient plate method as described in Example 9. The results are shown in TABLE 3.

TABLE 3

| | MIC/(µg/ml) | | | |
|---|---|---|---|---|
| PLASMID | Tet | Cml | Amp | Rif |
| AG 102 mar mutant | 12.5 | 34.2 | 17.7 | 8.8 |
| AG 102 with marR+ plasmid | 3.7 | 3.3 | 5.5 | 1.1 |
| AG 102 with antisense-marA plasmid pKMN23 | 8.3 | 16.4 | 15 | 2.6 |

As shown above, the antisense construct reduced resistance to various unrelated antibiotics, hence proving that antisense sequences directed to sequences associated with the marORAB operon provide an ideal tool to inhibit bacterial drug resistance.

Figure 2:
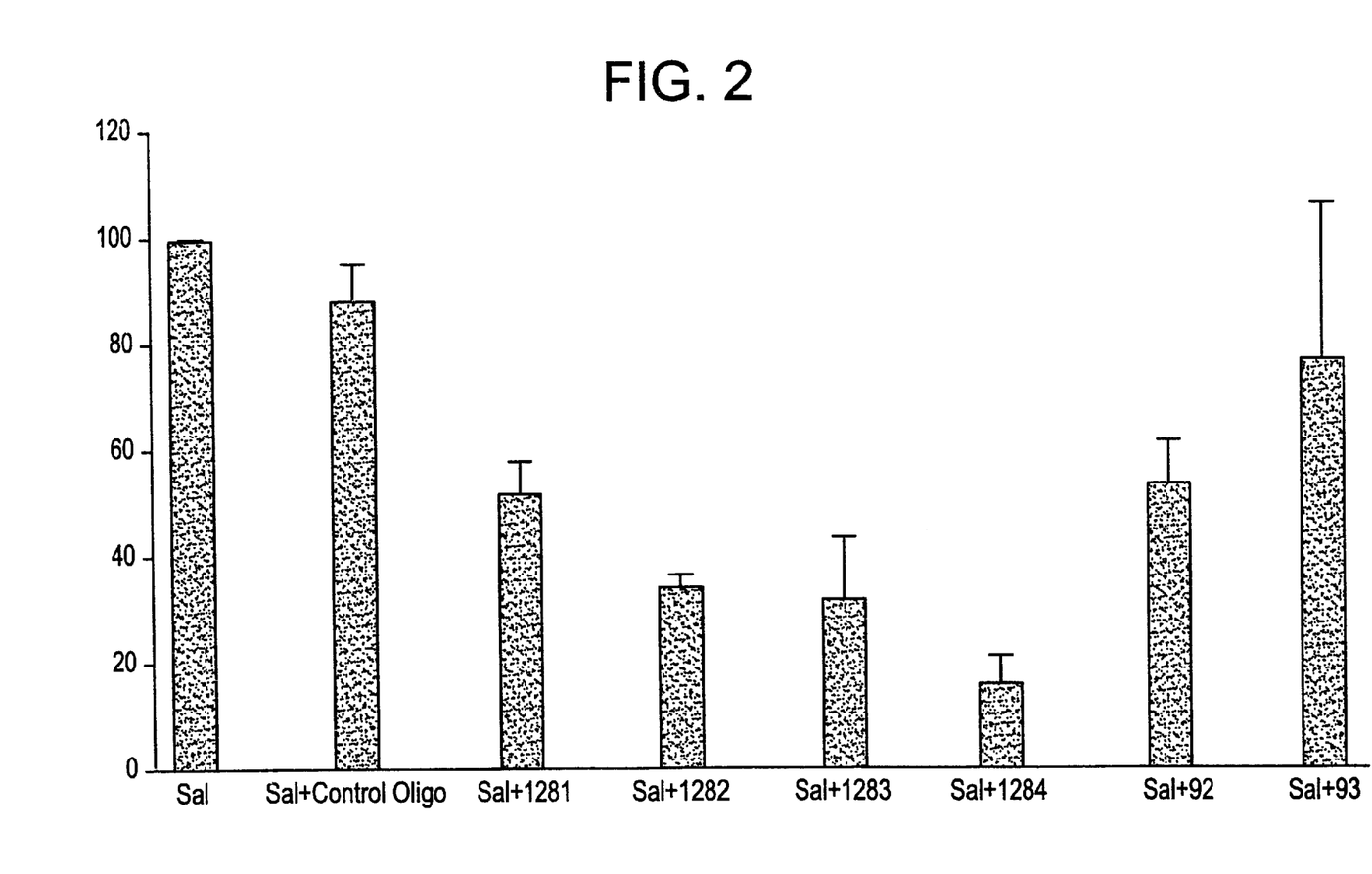
FIG. 2 is a graphic representation of the ability of representative antisense oligonucleotides of the invention to inhibit the expression of a marA::lacZ fusion in *E. coli*. The representative oligonucleotides are identified on the x axis, and the corresponding spectrophotometeric O.D. unit levels of β-galactosidase activities observed as a percent of the control in the absence of oligonucleotides are represented on the y axis.

To optimize the inhibitory effect of the antisense oligonucleotides, KMN18 cells (a marORA-lacZ fusion *E. coli* cell line described above) were incubated with increasing concentrations of antisense oligonucleotides (10–20 µM). Transcription of marA sequences was induced by the addition of sodium salicylate. Samples were assayed for β-galactosidase activity at 60 minute intervals. As shown in FIG. 2 all oligonucleotides added at 20 µM concentrations reduced marA-lacZ activity. Control oligonucleotide 101C (SEQ ID NO:7) showed no reduction in marA-lacZ activity. In addition, antisense oligonucleotides 92 (SEQ ID NO:1) and 1284 (SEQ ID NCO:6) reduced marA-lacZ activity from a cell line constitutively expressing a marORA-lacZ fusion protein (KMN14) (data not shown).

In order to ascertain the effects of increasing the oligonucleotides of the invention on the bactericidal activity of norfloxacin, competent cells of ML308-225-C2 (an isolated Mar mutant *E. coli* strain) were treated with increasing concentrations of representative antisense oligonucleotide 92 (SEQ ID NO:1), or oligonucleotide 1284 (SEQ ID NO:6), or control oligonucleotide 1403 (SEQ ID NO:8), (scrambled sequence of oligonucleotide 1284). TABLE 4 summarizes the results pertaining to antisense oligonucleotide 1284 in duplicate experiments.

TABLE 4

| NORFLOXACIN (µg/ml) | OLIGO 1284 (µM) | % OF CONTROL | CELLS |
|---|---|---|---|
| 0 | 0 | 100 | 100 |
| 0.5 | 0 | 71 | 57 |
| 0.5 | 20 | 43 | 54 |
| 0.5 | 40 | 42 | 58 |
| 0.5 | 100 | 27 | 46 |
| 0.5 | 200 | 25 | 38 |

As shown, the killing effect of norfloxacin against ML308-C2 was enhanced significantly by the addition of antisense oligonucleotide 1284 (SEQ ID NO:6).

In order to establish the effects of increasing oligonucleotide concentrations on the antibacterial activity of antibiotics, Mar mutant cells were treated with oligonucleotide 1284 (SEQ ID NO:6) at a final concentration of 20, 40, 100 and 200 mM in the presence of 0.5 mg/ml of norfloxacin for 1 hour. Cell growth in the presence of the various concentrations of oligonucleotide 1284 (SEQ ID NO:6) was compared to that observed in untreated cells. The results are shown in TABLE 5.

TABLE 5

| NORFLOXACIN mg/ml | [OLIGO 1284] mM | % OF CONTROL (untreated cells) |
|---|---|---|
| — | — | 100 |
| 0.5 | — | 65 |
| 0.5 | 20 | 48 |
| 0.5 | 40 | 50 |
| 0.5 | 100 | 36 |
| 0.5 | 200 | 31 |

As shown above for oligonucleotide 1284 (SEQ ID NO.6), the antisense oligonucleotides of this invention enhance the antibactericidal effect of antibiotics such as norfloxacin.

To ascertain that the inhibitory effect observed was a specific antisense effect causing the repression of the RNA message from the marORAB operon, the effect of oligonucleotide 1284 (SEQ ID NO:6) on bacterial growth was measured following one or two hours oligonucleotide treatment. Bacterial growth was compared to that observed following treatment with the scrambled negative control oligonucleotide 1403 (SEQ ID NO:8). Concentrations of 40 and 100 µM of antisense oligonucleotides 1284 and scrambled oligonucleotide 1403 were shown to cause no change in cell viability in the absence of antibiotic. These results demonstrate that the killing effect of oligonucleotide 1284 shown above in TABLE 4 is not the result of the presence of the oligonucleotide alone, but rather, is the result of the combined action of the antibactericidal agent and the marORAB oligonucleotide of the invention.

The following examples illustrate the preferred modes of making and practicing the present invention, but are not meant to limit the scope of the invention since alternative methods may be utilized to obtain similar results.

EXAMPLE 1

Preparation of Oligonucleotides

Synthesis of the following phosphothioate oligonucleotides: 92 (SEQ ID NO:1), 93 (SEQ ID NO:2), 1281 (SEQ ID NO:3), 1282 (SEQ ID NO:4), 1283 (SEQ ID NO:5), 1284 (SEQ ID NO:6), 101C (SEQ ID NO:7), 1403 (SEQ ID NO:8), RK1, (SEQ ID NO:9), A2, (SEQ ID NO:10), LZ, (SEQ ID NO:11), ORAB2, (SEQ ID NO:12), and RK3, (SEQ ID NO:13) was performed on a synthesizer (Pharmacia Gene Assembler Series Synthesizer, Pharmacia LKB Biotechnology, Uppsalt, Sweden) using standard b-cyanoethylphosphoramidite procedure (see, Sonveaux "Protecting Groups in Oligonucleotides Synthesis" in Agrawal (1994) *Methods in molecular Biology* 26:1–72; see also Uhlmann et al. (1990) Chem. Rev. 90:543–583). Agarwal ) and amidites (Cruachem, Glasgow, Scotland) and supports (Millipore, Bedford, Mass.). The random 20-mer phosphodiester contained an equimolar mixture of A, C, G, and T at each position. DNAs were deprotected by treatment of the support with 1 ml of acqueous NaOH at 55° C. for 16 hours. Subsequently the ammonia was removed from the support, the support was washed with 200 ml of water, and the two fractions were pooled and lyophilized. Following assembly and deprotection, the oligonucleotides were ethanol precipitated twice, dried, and suspended in phosphate-buffered saline (PBS) at the desired concentration.

The purity of these oligonucleotides was tested by capillary gel electrophoreses and ion exchange HPLC. Endotoxin levels in the oligonucleotide preparation was determined using the Luminous Amebocyte Assay (Bang (15953) *Biol. Bull.* (Woods Hole, Mass.) 105:361–362).

EXAMPLE 2

Preparation of Constructs

A. Selection of a Mar Mutant of ML308-225

Antibiotic resistant mutants of ML308-225 (Rahman et al. (1991) *Antisense Res. Dev.* 1:319–327) were grown and maintained at 30° C. in LB broth. These mutants were selected by spreading washed overnight cultures onto a LB agar plate containing chloramphenicol (5 μg/ml, Sigma, St. Louis, Mo.) and incubated at 30° C. for 48–72 hours. Single colonies appearing after 48 hours were picked for further study. Resistant colonies were observed for multiple antibiotic resistance using antibiotic gradient plates.

One mutant showing increased minimal inhibitory concentrations (hereinafter referred to as MIC) to tetracycline, chloramphenicol, ampicillin, nalidixic acid, and norfloxacin was selected and designated ML308-C2. Sequencing confirmed a C ® T substitution in amino acid 117 of marR, which results in a truncated MarR protein. When wild type marR (pMAL-marR) was cloned into ML308-C2, the MIC's decreased to that of levels expressed by the wild-type ML308-225 strain (unpublished data). Northern analysis using a marA DNA probe confirmed that ML308-C2 over expresses marA and was a Mar mutant (unpublished data). These results, in conjunction with the sequence data, support the conclusion that a marR mutation is responsible for the Mar phenotype in the ML308-C2 strain.

B. Construction of pDW10 and pDW11

Plasmid DNA was prepared using the Promega Wizard™ Prep Kit (Madison, Wis.). Restriction endonucleases and T4 DNA ligase (New England Biolabs, Beverly, Mass.) were used under conditions suggested by the supplier. PCR amplification was carried out using the Perkin Elmer Cetus DNA thermal cycler 480. Taq Polymerase and reagents (Perkin Elmer Cetus, Norwalk, Conn.) were used as directed to amplify the target sequence. Based on the known DNA sequence of the mar loci (GenBank accession #M96235), PCR primers were created which flanked the coding sequence and allowed amplification of marA and the marORAB operon region, which were then cloned behind the T7 promoter of pBLUESCRIPT KS (Stratagene, La Jolla, Calif.). The marA PCR primers were designed to amplify the marA coding sequence from 1893–2282 bp, resulting in a 389 bp product. A marORAB PCR product (1281 bp) was created as well using primers designed to amplify the DNA sequence of marORAB from 1311–2592 bp from the published sequence. Restriction endonuclease sites for EcoR1 and Pst1 were incorporated into the ends of PCR primers to ensure that insertion of fragments were in the correct orientation when cloned into pBLUESCRIPT. pBLUESCRIPT-marA was termed pDW10 and pBLUESCRIPT-marORAB was named pDW11. To ensure that the proper DNA fragments were cloned, the DNA sequence of the cloned PCR products was determined by the method of Sanger et al. (*Proc. Natl. Acad Sci. USA* (1977) 74:5463–5467) using the Sequenase™ sequencing kit (U.S. Biochemical, Cleveland, Ohio).

EXAMPLE 3

Transcription of Target RNA

Ten μg each of the plasmids pDW10 (marA) and pDW11 (marORAB) were linearized with HindIII (New England Biolabs, Beverly, Mass.) or EcoRI (New England Biolabs, Beverly, Mass.) in a 50 μl reaction containing a 1X dilution of the appropriate buffer supplied and 100 U of restriction enzyme. Cleavage was allowed to proceed at 37° C. for 2 hrs. After this time the reaction was extracted twice with buffered phenol/CHC13 (1:1), twice with $CHCl_3$/isoamyl alcohol (24:1), and precipitated with 3 volumes of precipitation mix (66 mM sodium acetate in ethanol). The DNA was collected by centrifugation in a microfuge for 20 min, washed with 70% ethanol, and dried briefly under vacuum. The resultant pellet was resuspended in 20 μl of water and stored frozen until needed.

RNA bearing a hydroxyl group was transcribed from the linearized plasmids in a 20 μl reaction containing IX supplied buffer, 1 mM each of rATP, rCTP, rUTP, 0.9 mM guanosine, 0.1 mM GTP, 2 U/ml RNasin (Promega, Madison, Wis.), 2 μg linearized plasmid, and 2.5 μl of 50,000 U/ml T7 RNA polymerase (New England Biolabs, Beverly, Mass.), added in the order indicated. This reaction was incubated at 37° C. for 1 hr and 1 unit of RQ1 DNase (Promega, Madison, Wis.) was added. DNA was allowed to digest at 37° C. for 15 min and then the RNA was purified using a ProbeQuant G-50 spin column (Pharmacia Biotech, Piscataway, N.J.) and the manufacturer's protocol. This produced about 50 μl of solution containing the marORAB transcript. At this point, the integrity of an aliquot of the transcript was checked by electrophoresis on a 1% agarose TBE gel and ethidium bromide staining.

EXAMPLE 4

Radiolabelling of Target RNA

The transcripts were radiolabelled with $^{32}P$ in a 20 μl reaction containing 10 μl of transcript (⅕th of transcription), 2 μl of supplied T4 polynucleotide kinase buffer, 5 μl of g-$^{32}P$-ATP (10 mCi/ml, Amersham, Cleveland, Ohio), 1 μl of 40 U/ml RNasin, and 2 μl of 10 U/μl T4 polynucleotide kinase (New England Biolabs, Beverly, Mass.). After 1 hr of incubation at 37° C., the transcript was purified using a spin column as described above, yielding the radiolabelled transcript in a volume of approximately 50 μl. Integrity of the transcript was checked by denaturing polyacrylamide electrophoresis and autoradiography.

EXAMPLE 5

RNase H Mapping of Accessible Sites in Target RNA

Mapping of sites accessible to oligonucleotide binding using RNase H as a probe for RNA/DNA duplex was done in a 10 μl reaction containing 5 μl of radiolabelled transcript, 1 μl of 10X RNase H buffer (400 mM Tris-HC1, pH 7.4, 40 mM $MgCl_2$, 10 mM dithiothreitol), 0.5 ml of 40 U/μl RNasin, 1 μl of 500 mM random 20-mer (heated and snap cooled), and 1.5 μl of water. This mixture was incubated at room temperature for 90 min and 1 μl of 1 U/ml RNase H (Boehringer Mannheim, Indianapolis, Ind.) was added. This constitutes the complete reaction. Control reactions lacking either random 20-mer, RNase H, or both were done in parallel. After 10 min at room temperature, the reaction was quenched by the addition of 10 μl of formamid loading dye. Samples were denatured by heating to 95° C. for 5 min and 7 μl were analyzed by electrophoresis on a 4% polyacrylamide denaturing gel. Accessible sites were identified as abundant radiolabelled fragments unique to the complete reaction lane. Lengths of RNA fragments produced were calculated by comparison to a radiolabelled DNA restriction ladder. This ladder had been previously calibrated against RNAs of known lengths.

Sites accessible to oligonucleotide binding were found in both the 5' untranslated region (bases 1401–1450) and the coding region (bases 1708–1727) of MarR as well as near the translational start (bases 1890–1950) and in the coding region (bases 2040–2075) of MarA (numbering as in Gasparro et al. (1991) *Antisense Res. Dev.* 1:117–140).

EXAMPLE 6

Construction of Chromosomal marA-lacZ and marORA-lacZ Fusions

A translational fusion plasmid (pMLB1034) and a transcriptional fusion plasmid (pMBL1109) were used for constructing marA-lacZ fusions. A 818 bp DraI fragment, containing marOR and 144 bp of marA, were cloned into the SmaI site of the fusion plasmids. The resulting plasmids, pKMN14 and pKMN18 have the marA fusion in the same translation frame with lacZ. Plasmids pKMN19 and pKMN21 have marA inserted in a position upstream of a promoterless lacZ gene, thereby creating a transcriptional fusion. The marOR(A) fragment of pKMN14 and pKMN19 were derived from the pHTHM191 plasmid which has a missense mutation at the 45th amino acid of marR, while pKMN18 and pKMN21 contained marOR(A) from the wild type pHHM183 plasmid. A 560 bp fragment bearing the XmnI site in marR to the DraI site in marA was also inserted into the fusion plasmids leading to pKMN16, a marA-lacZ translational fusion plasmid and pKMN21, a marA-lacZ transcriptional fusion plasmid.

The marOR*A-lacZ, marORA-lacZ, and mar(R)A-lacZ, translational fusions in plasmids pKMN14, pKMN18, and pKMN16 respectively were transduced via a site specific recombination mechanism into the chromosome of ASS111, which contains a 1.24 kb marORAB deletion and is lacZ$^-$, phoA$^-$, and recA. First, the fusion plasmids were transformed individually into ASS110, a recA$^+$ strain (Seone, A. et al. (1996) *J. Bacteriol.* 177:530–535). The transformants were infected with λRZ5 to allow the formation of λRZ5 (marA-lacZ) recombinants. The recombinant lysate was used to transduce the plasmid less ASS110 strain and ampicillin resistant (50 μg/ml) lysogens were selected. Lysates from these purified lysogens were th(en used to infect ASS111.

The presence of the marA-lacZ fusion in the chromosomal DNA of ampicillin resistant lysogenies was confirmed by PCR for the marR-lacZ fragment and the marA-lacZ fragment. Primer RK1 (5'-GTGAAAAGTA CCAGCGATCTG-3'; SEQ ID NO:9), which can hybridize to the 5' terminal end of marR was used for the marR-lacZ fragment amplification and primer A2 (5'-GGTGAATTCATGACGATGTCCAGACGC-3'; SEQ ID NO:10), which can hybridize to the 5' terminal end of marA, was used for marA-lacZ fragment amplification. Primer LZ (5'-ATGTGCTGCAAGGCGAT-3'; SEQ ID NO:11), which can anneal to the internal portion of lacZ, was used as the lacZ primer in both constructions.

EXAMPLE 7

Cloning of marR and Antisense marA Under lac and T7 Promoters

Primer ORAB2 (5'-GGACTGCAGGCTAG CCTTGCATCGCAT-3'; SEQ ID NO:12) hybridizes with nucleotides 1311 to 1328 in marO ((Gen Bank sequence #M96235) and create a PstI site. Primer RK3 (5'-TCTTGAATTCTTACGGCAGGACTTTCTTAAG-3'; SEQ ID NO:13) hybridizes with nucleotides 1858 to 1879 at the 3' terminal end of marR and (create an EcoR1 site. These primers were used for amplification of the marOR gene from the wild type AG100 *E. coli* strain and the Mar mutant AG102 strain. The resulting 570 bp Pst1-EcoR1 PCR fragments were cloned into the Pst1-EcoR1 site of the pSPOK plasmid, a kanamycin resistant derivative of pSPORTI (Gibco/BRL, Washington, D.C.), (Manneewannakul et al. (1994) supra). The marOR/pSPOK plasmid can be induced for the expression of the marR gene from either the lac or T7 promoter by IPTG or T7 RNA polymerase, respectively.

A 473 bp fragment from the SacII site in marR to the Dra1 site in marA was inserted into the SnaB1 site of pSPOK. The resulting construct, pKMN23, in which the marA gene was directed in the opposite orientation of the lac promoter in pSPOK, was selected for the antisense marA construct. MarA was fused to lacZ in both transcriptional and translational fusions using cloning vectors pMLB1034 or pMLB1109). The fusions were introduced into a previously described mar deleted strain. Additionally, a 473 bp segment consisting of 330 bases of marR and 143 bases of marA was cloned in the antisense direction behind the lac promoter/T7 polymerase system (creating pKMN23).

EXAMPLE 8

DNA Transformation and Oligonucleotide Treatment of *E. coli*

DNA transformation into bacterial strains was performed using the $CaCl_2$ procedure as previously described by Cohen et al. *J. Bacteriol.* (1993) supra) or via electroporation. Competent cells ($10^5$) were transferred to tubes containing marORAB or control oligonucleotides in various concentrations. Oligonucleotide uptake was induced by a 1 minute heat shock (42° C.) or through electroporation and the samples were incubated at 30° C. for 1 or 2 hours. Depending on the experiment, strains incubated with the oligonucleotides were used in μ-galactosidase assays, or colony formation and/or time kill experiments.

EXAMPLE 9

Gradient Plate Assay

Bacterial susceptibility to tetracycline hydrochloride, chloramphenicol, ampicillin, kanamycin, rifampin, nalidixic acid and norfloxacin was assayed by the gradient plate method. (*Microbiology: Including Immunology and Molecular Genetics* (3rd ed.)(Davis et al. eds.(1980) J. P. Lippincott Co., Philadelphia, Pa.).

EXAMPLE 10

β-galactosidase Assays

Strains KMN14 and KMN18, with or without antisense oligonucleotides, were grown at 30° C. to mid-logarithmic phase. Fifty microliters of competent cells were treated with the appropriate oligonucleotide, heat shocked for 1 minute, and incubated at room temperature for 30 minutes to allow for annealing of the oligonucleotide with the mRNA. LB broth was then added to 1 ml, and the cell/oligonucleotide mixture was then incubated at 30° C. for 30 minutes. After 30 minutes incubation, KMN18 (wild type) was induced with 5 mM sodium salicylate, whereas KMN14 was not (constitutively expressed mar mRNA). Samples of cell/oligonucleotide mixtures were then removed at 1 hour intervals and assayed for P-galactosidase the method of Miller (*Immunochemistry* (1972) 9:217–228).

EXAMPLE 11

Inhibition of β-galactosidase Activity in KMN18

The marA transcript was inducible with 5 mM sodium salicylate after 30 minutes incubation in *E. coli* KMN18 strain (a marORA-lacZ fusion cell line). KMN18 was incubated with increasing concentrations (4–20 μM) of antisense oligonucleotides. The cells were then induced with 5 mM salicylate. The samples were removed after 30 and 60 minute intervals and assayed for β-galactosidase activity. After 30 and 60 minute incubations with salicylate, oligonucleotides 92 and 1284 at 20 μM concentrations caused reduced marA-lacZ activity (FIG. 2). Control Oligonucleotide 101 showed no reduction in marA-lacZ activity. At 20 μM, the same and an additional oligonucleotide, 1403, a scrambled 1284, were tested. In four separate experiments oligonucleotides 92 and 1284 showed significant activity. These studies showed that antisense oligonucleotides 92 and 1284 showed a dose response effect on LacZ expression.

EXAMPLE 12

Augmentation of Bactericidal Activity of Norfloxacin Using marORAB-specific Oligonucleotides Competent cells of ML308-225-C2 (Mar mutant)(50 μl, $10^7$ cells) were incubated with increasing concentrations of antisense oligonucleotides 1403, 92, or 1284 for 30 minutes on ice. The cell/oligonucleotide mixture was either heat shocked at 42° C. for one minute or electroporated (to allow for uptake). The cell suspension was placed on ice for two minutes and then placed at room temperature for 30 minutes to allow for association of the antisense oligonucleotide with the mRNA. LB broth (450 μl) was added to the mixture which was incubated for 1 and 2 hours at 30° C. After 30 minutes of incubation at 30° C., 1X the MIC of norfloxacin (0.5 μg/ml) was added to the cell suspension. At 1 hour post exposure to norfloxacin, 100 μl aliquots of cell/oligonucleotide mixtures were collected, diluted into PBS and the various dilutions were plated on LB agar plates. Following overnight incubation at 30° C., the number of colonies was counted on al plates. For all experiments, the samples were plated in duplicate or triplicate and all colonies on a plate were counted.

Antisense oligonucleotide 1284 (SEQ ID NO:6) enhanced the killing effect of norfloxacin against ML308-C2 as shown above in TABLE 4. In two separate experiments, there was a greater effect with 100–200 μM vs. 20–40 μM oligonucleotide. Oligonucleotide 1284 was then compared to its scrambled control 1403 (SEQ ID NO:8) to determine if its activity was a specific antisense effect directed at repressing the marRAB RNA message Concentrations of 40 and 100 μM were chosen based on the results of TABLE 4. As shown in TABLE 5 the presence of control Oligonucleotide 1403 alone caused no change in cell viability. At 1 hour post exposure to 1X MIC of norfloxacin, 1284 exhibited a 23% drop in viability as compared to 6% with 1403. This effect seemed to diminish at 2 hours. The results showed a specific effect of oligonucleotide 1284 in enhancing the killing effects of norfloxacin against a mar mutant which had been resistant to the bactericidal effect of norfloxacin.

Equivalents

Those skilled in the art will recognize, or be able to ascertain, using no more than routine experimentation, numerous equivalents to the specific substances and procedures described herein. Such equivalents are considered to be within the scope of this invention, and are covered by the following claims.

---

What is claimed is:

1. An oligonucleotide complementary to a transcript of the marORAB operon, wherein said oligonucleotide comprises a nucleotide sequence selected from the group consisting of: the nucleotide sequence shown in SEQ. NO:1, SEQ. ID NO:2, SEQ. ID NO:3, SEQ. ID NO:4, SEQ. ID NO:5, and SEQ. ID NO:6 said oligonucleotide having from about 15 to about 50 nucleotides and wherein said oligonucleotide inhibits expression of the operon.

2. The oligonucleotide of claim 1 wherein the oligonucleotide contains at least one internucleotide linkage selected from the group consisting of alkylphosphonates, phosphorothioates, phosphorodithioates, alkylphosphonothioates, phosphoramidates, phosphate esters, carbamates, acetamidate, carboxymethyl esters, carbonates, and phosphate triesters.

3. The oligonucleotide of claim 2 wherein the oligonucleotide contains at least one phosphorothioate internucleotide linkage.

4. The oligonucleotide of claim 1 comprising at least one deoxyribonucleotide.

5. The oligonucleotide of claim 1 comprising at least one ribonucleotide.

6. The oligonucleotide of claim 4 comprising at least one ribonucleotide.

7. The oligonucleotide of claim 1 wherein the oligonucleotide is a synthetic oligonucleotide and is from about 15 to about 21 nucleotides in length.

8. The oligonucleotide of claim 1 wherein said oligonucleotide consists of a nucleotide sequence selected from the group consisting of: the nucleotide sequence shown in SEQ. ID NO:1, SEQ. ID NO:2, SEQ. ID NO:3, SEQ. ID NO:4, SEQ. ID NO:5, and SEQ. ID NO:6.

9. A method of inhibiting expression of the marORAB operon comprising the step of contacting a transcript of the marORAB operon nucleic acid with an oligonucleotide complementary to the transcript wherein said oligonucleotide comprises a nucleotide sequence selected from the group consisting of: the nucleotide sequence shown in SEQ. ID NO:1, SEQ. ID NO:2, SEQ. ID NO:3, SEQ. ID NO:4, SEQ. ID NO:5, and SEQ. ID NO:6 and wherein said oligonucleotide has from about 15 to about 50 nucleotides.

10. The method of claim 9 wherein the oligonucleotide consists of a nucleotide sequence selected from the group consisting of SEQ. ID NO:1, SEQ. ID NO:2, SEQ. ID NO:3, SEQ. ID NO:4, SEQ. ID NO:5, and SEQ. ID NO:6.

11. A method of reducing bacterial resistance to an antibiotic comprising contacting a bacterium with at least one oligonucleotide complementary to a transcript of the marORAB operon wherein said oligonucleotide comprises a nucleotide sequence selected from the group consisting of: the nucleotide sequence shown in SEQ. ID NO:1, SEQ. ID NO:2, SEQ. ID NO:3, SEQ. ID NO:4, SEQ. ID NO:5, and SEQ. ID NO:6, and wherein said oligonucleotide has from about 7 to about 50 nucleotides such that bacterial resistance to an antibiotic is reduced.

12. The method of claim 11, further comprising contacting the bacterium with at least one antibiotic.

13. The method of claim 12, wherein the antibiotic is selected from the group consisting of: a penicillin, a cephalosporin, an aminoglycoside, a sulfonamide, a macrolide, a tetracycline, a lincoside, a quinolone, a chloramphenicol, a vancomycin, a rifampin, an isoniazid, or a trimethoprim.

14. The method of claim 11, wherein the oligonucleotide consists of a nucleotide sequence selected from the group consisting of SEQ. ID NO:1, SEQ. ID NO:2, SEQ. ID NO:3, SEQ. ID NO:4, SEQ. ID NO:5, and SEQ. ID NO:6.

15. The method of claim 11, wherein the bacterium is exposed to at least two oligonucleotides having a nucleotide sequence selected from the group consisting of SEQ. ID NO:1, SEQ. ID NO:2, SEQ. ID NO:3, SEQ. ID NO:4, SEQ. ID NO:5, and SEQ. ID NO:6.

16. The method of claim 11, wherein the bacterium is a species selected from the group consisting of Escherichia, Salmonella, Shigella, Klebsiella, Citrobacter, Hafnia, and Enterobacter.

17. A composition comprising a synthetic oligonucleotide complementary to a transcript of a marORAB operon which inhibits the expression of a locus in the operon, wherein the oligonucleotide comprises a nucleotide sequence selected from the group consisting of SEQ. ID NO:1, SEQ. ID NO:2, SEQ. ID NO:3, SEQ. ID NO:4, SEQ. ID NO:5, and SEQ. ID NO:6, said oligonucleotide having from about 15 to about 50 nucleotides, and a physiologically acceptable carrier.

18. The composition of claim 17 wherein the oligonucleotide consists of a nucleotide sequence shown in SEQ: ID NO:1, SEQ. ID: NO:2, SEQ. ID NO:3, SEQ. ID NO:4, SEQ. ID NO:5, or SEQ. ID NO:6.

19. The oligonucleotide of claim 1 wherein the oligonucleotide is from about 15 to about 35 nucleotides in length.

20. The method of claim 9 wherein the oligonucleotide is from about 15 to about 35 nucleotides in length.

21. The composition of claim 17 wherein the oligonucleotide is from about 15 to about 35 nucleotides in length.

* * * * *

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
      (A) LENGTH: 18 base pairs
      (B) TYPE: nucleic acid
      (C) STRANDEDNESS: single
      (D) TOPOLOGY: linear    (ii) MOLECULE TYPE: cDNA (xi) SEQUENCE DESCRIPTION: SEQ ID NO:1:

GCGTCTGGAC ATCGTCAT                                                     18

(2) INFORMATION FOR SEQ ID NO:2:

(i) SEQUENCE CHARACTERISTICS:
         (A) LENGTH: 15 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:2:

ATCGTCATAG CTCTT                                                        15

(2) INFORMATION FOR SEQ ID NO:3:

(i) SEQUENCE CHARACTERISTICS:
         (A) LENGTH: 19 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:3:

CTTTTCACAT TAGTTGCCC                                                    19

(2) INFORMATION FOR SEQ ID NO:4:

(i) SEQUENCE CHARACTERISTICS:
         (A) LENGTH: 19 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:4:

GCGCTTGTCA TTCGGGTTC                                                    19

(2) INFORMATION FOR SEQ ID NO:5:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:5:

GTAATTAGTT GCAGAGGATA                                                   20

(2) INFORMATION FOR SEQ ID NO:6:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:6:

TAGTTGCAGG AGATAATATT G                                                 21

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear     (ii) MOLECULE TYPE: cDNA     (xi) SEQUENCE DESCRIPTION: SEQ ID NO:7:

CTGACTGCCA ACTATGAACA                                  20

(2) INFORMATION FOR SEQ ID NO:8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear     (ii) MOLECULE TYPE: cDNA     (xi) SEQUENCE DESCRIPTION: SEQ ID NO:8:

GTTCAGAGTT AGTAGGAATA T                                21

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear     (ii) MOLECULE TYPE: cDNA     (xi) SEQUENCE DESCRIPTION: SEQ ID NO:9:

GTGAAAAGTA CCAGCGATCT G                                21

(2) INFORMATION FOR SEQ ID NO:10:

(i) SEQUENCE CHARACTERISTICS:
        (A) LENGTH: 27 base pairs
        (B) TYPE: nucleic acid
        (C) STRANDEDNESS: single
        (D) TOPOLOGY: linear     (ii) MOLECULE TYPE: cDNA     (xi) SEQUENCE DESCRIPTION: SEQ ID NO:10:

GGTGAATTCA TGACGATGTC CAGACGC                          27

(2) INFORMATION FOR SEQ ID NO:11:

(i) SEQUENCE CHARACTERISTICS:
        (A) LENGTH: 17 base pairs
        (B) TYPE: nucleic acid
        (C) STRANDEDNESS: single
        (D) TOPOLOGY: linear     (ii) MOLECULE TYPE: cDNA     (xi) SEQUENCE DESCRIPTION: SEQ ID NO:11:

ATGTGCTGCA AGGCGAT                                        17

(2) INFORMATION FOR SEQ ID NO:12:

(i) SEQUENCE CHARACTERISTICS:

-continued

```
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

GGACTGCAGG CTAGCCTTGC ATCGCAT                                               27

(2) INFORMATION FOR SEQ ID NO:13:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

TCTTGAATTC TTACGGCAGG ACTTTCTTAA G                                          31
```